United States Patent [19]

Krämer et al.

[11] 4,207,328
[45] Jun. 10, 1980

[54] 1-PHENOXY-2-(2,4-DICHLOROPHENYL)-1-IMIDAZOL-1-YL-ETHAN-2-ONES AND -OLS AND ANTIMYCOTIC AND FUNGICIDAL USE

[75] Inventors: Wolfgang Krämer; Karl H. Büchel; Manfred Plempel, all of Wuppertal; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 872,987

[22] Filed: Jan. 27, 1978

[30] Foreign Application Priority Data

Feb. 11, 1977 [DE] Fed. Rep. of Germany ....... 2705676
Feb. 11, 1977 [DE] Fed. Rep. of Germany ....... 2705677

[51] Int. Cl.$^2$ .................. A61K 31/415; C07D 233/60
[52] U.S. Cl. .................................. 424/273 R; 548/341
[58] Field of Search ...................... 548/341; 424/273 R

[56] References Cited

U.S. PATENT DOCUMENTS

| | | | |
|---|---|---|---|
| 3,812,142 | 5/1974 | Meiser et al. | 548/341 |
| 3,940,414 | 2/1976 | Kramer et al. | 548/341 |
| 3,968,229 | 7/1976 | Kramer et al. | 424/273 |

*Primary Examiner*—Richard Raymond

[57] ABSTRACT

This invention relates to new 2,4-dichlorophenyl-imidaziolyl-ethan-ones and -ols useful as antimycotic and fungicidal agents. The compounds are useful as medicaments as well as in the plant protection area.

20 Claims, No Drawings

1-PHENOXY-2-(2,4-DICHLOROPHENYL)-1-IMIDAZOL-1-YL-ETHAN-2-ONES AND -OLS AND ANTIMYCOTIC AND FUNGICIDAL USE

The present invention relates to certain new imidazolyl compounds, to a process for their preparation and their use as medicaments, for warm-blooded animals in particular as antimycotics; the new imidazolyl compounds are also useful because of their powerful fungicidal properties in the plant protection area.

It has already been disclosed that phenoxy-imidazolyl derivatives have a good antimycotic action (compare German Offenlegungsschriften (German Published Specifications) Nos. 2,105,490 and 2,333,355. However, their action, in particular against dermatophytes and in vivo against Candida, is not always completely satisfactory.

It has now been found that the new compounds which are 2,4-dichlorophenylimidazolyl-ethan-ones and -ols of the general formula

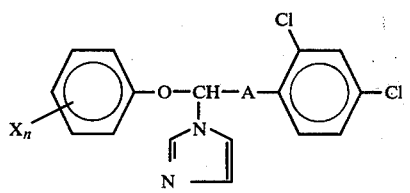

in which
A is a keto group or a CH(OH) group,
X is halogen, straight-chain or branched alkyl with 1 to 4 carbon atoms or phenyl optionally substituted by halogen preferably chlorine, and
n is an integer from 0 to 3, preferably from 0 to 2,
and their salts have powerful antimycotic properties.

Among the new imidazolyl ethanone and ethanol salts of the invention, those salts that are pharmaceutically acceptable are particularly important and preferred.

Those compounds in which in formula (I) A represents the CH(OH) group possess two asymmetric carbon atoms; they can therefore exist in the form of both geometric isomers (erythro form and threo form), which can be obtained in various proportions. In both cases, they exist in the form of optical isomers. All the isomers are included within the scope of the present invention.

Racemate mixtures can be separated into the pure racemates in a known manner on the basis of the physicochemical differences of the constituents, for example by chromatography and/or fractional crystallisation.

Pure racemates can be resolved according to known methods, for example by recrystallisation from an optically active solvent, with the aid of micro-organisms or by reaction with an optically active acid or base which form salts with the racemic compound and separation of the salts obtained in this manner, for example on the basis of their different solubilities, into the diastereomers from which the antipodes can be liberated by the action of suitable agents. Particularly customary optically active acids, are, for example, the d- and α-forms of tartaric acid, di-o-toluyltartaric acid, malic acid. Suitable optically active bases are, for example, optically active α-phenylethylamine, α-(1-naphthyl)-ethylamine, quinone, cinchonidine and brucine. Advantageously, the more active of the two antipodes is isolated.

According to the invention it is however also possible to obtain the end products in the form of the pure racemates or optical antipodes by employing starting substances, containing one or more asymmetrical C atoms, in the form of the pure racemates or optical antipodes.

In a further aspect the present invention provides a process for the preparation of a compound according to the invention in which a 1-bromo-2-(2,4,-dichlorophenyl)-1-phenoxy-ethan-2-one of the general formula

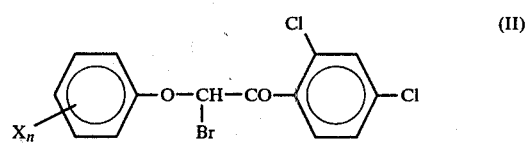

in which
X and n have the same meaning as defined above in formula I, is reacted with imidazole in the presence of a diluent and an acid-binding agent, and where desirable the resulting imidazolyl-ethanone compound is reduced with a complex borohydride or an equivalent reducing agent, optionally in the presence of a diluent so as to produce the corresponding imidazolyl-ethanol compound of Formula I.

The new 2,4-dichlorophenyl-imidazolyl-ethan-ones and -ols of the general Formula I and their salts can be interconverted in any suitable manner; methods for such interconversion are known in the art. For example salts may be prepared by reaction of the corresponding free compounds with acids.

Surprisingly, the active compounds according to the invention exhibit a better antimycotic, therapeutically useful activity than phenoxy-imidazolyl derivatives known from the state of the art, which are the most closely related compounds chemically and from the point of view of their action.

If 1-bromo-1-(4-chlorophenoxy)-2-(2,4-dichlorophenyl)-ethan-2-one and imidazole are used as starting materials, the course of the reaction can be represented by the following equation:

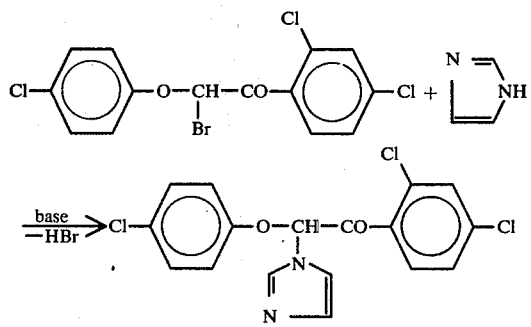

If 1-(4-chlorophenoxy)-2-(2,4-dichlorophenyl)-1-imidazol-1-yl)-ethan-2-one and sodium borohydride are used as starting substances, the course of the reaction can be represented by the following equation:

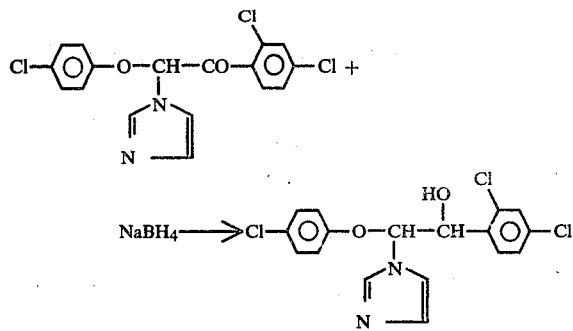

Examples of starting compounds of formula (II) which may be mentioned are: 1-bromo-1-phenoxy-2-(2,4-dichlorophenyl)-ethan-2-one, 1-bromo-1-(4-chlorophenoxy)-2-(2,4-dichlorophenyl)-ethan-2-one, 1-bromo-1-(4-fluorophenoxy)-2-(2,4-dichlorophenyl)-ethan-2-one, 1-bromo-1-(4-bromophenoxy)-2-(2,4-dichlorophenyl)-ethan-2-one, 1-bromo-(4-iodophenoxy)-2-(2,4-dichlorophenyl)-ethan-2-one, 1-bromo-1-(2,4-dichlorophenoxy)-2-(2,4-dichlorophenyl)-ethan-2-one, 1-bromo-1-(2,6-dichlorophenoxy)-2-(2,4-dichlorophenyl)-ethan-2-one, 1-bromo-1-(2,5-dichlorophenoxy)-2-(2,4-dichlorophenyl)-ethan-2-one, 1-bromo-1-(3-fluorophenoxy)-2-(2,4-dichlorophenyl)-ethan-2-one, 1-bromo-1-(3-chlorophenoxy)-2-(2,4-dichlorophenyl)-ethan-2-one, 1-bromo-1-(3-bromophenoxy)-2-(2,4-dichlorophenyl)-ethan-2-one, 1-bromo-1-(2-chlorophenoxy)-2-(2,4-dichlorophenyl)-ethan-2-one, 1-bromo-1-(4-methylphenoxy)-2-(2,4-dichlorophenyl)-ethan-2-one, 1-bromo-1-(4-ethylphenoxy)-2-(2,4-dichlorophenyl)-ethan-2-one, 1-bromo-1-(3-methylphenoxy)-2-(2,4-dichlorophenyl)-ethan-2-one, 1-bromo-1-(2-methylphenoxy)-2-(2,4-dichlorophenyl)-ethan-2-one, 1-bromo-1-(2-isopropylphenoxy)-2-(2,4-dichlorophenyl)-ethan-2-one, 1-bromo-1-(4-chloro-2-methylphenoxy)-2-(2,4-dichlorophenyl)-ethan-2-one, 1-bromo-1-(4-bromo-2-methylphenoxy)-2-(2,4-dichlorophenyl)-ethan-2-one, 1-bromo-1-(4-fluoro-2-methylphenoxy)-2-(2,4-dichlorophenyl)-ethan-2-one, 1-bromo-1(4-iodo-2-methylphenoxy)-2-(2,4-dichlorophenyl)-ethan-2-one, 1-bromo-1-(2,3-dimethylphenoxy)-2-(2,4-dichlorophenyl)-ethan-2-one, 1-bromo-1-(4-biphenylyloxy)-2-(2,4-dichlorophenyl)-ethan-2-one, 1-bromo-1-(4-4'-chlorobiphenylyloxy)-2-(2,4-dichlorophenyl)-ethan-2-one, 1-bromo-1-(4-2', 4'-dichlorobiphenylyloxy)-2-(2,4-dichlorophenyl)-ethan-2-one, 1-bromo-1-(4-2,4'-dichlorophenylyloxy)-2-(2,4-dichlorophenyl)-ethan-2-one, 1-bromo-1-(4-4'-bromobiphenylyloxy)-2-(2,4-dichlorophenyl)-ethan-2-one and 1-bromo-1-(4-2-chlorobiphenylyloxy)-2-(2,4-dichlorophenyl)-ethan-2-one.

The 1-bromo-2-(2,4-dichlorophenyl)-1-phenoxyethan-2-ones of the formula (II) to be used as starting compounds are not yet known, but they can be prepared by known processes by reacting known phenols of the formula

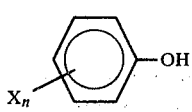

(III)

in which

X and n have the same meaning as defined above, in formula I with bromoacetophenone of the formula

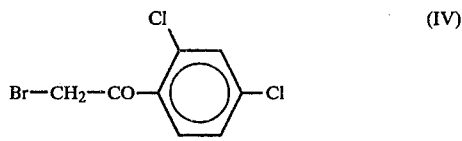

(IV)

The active hydrogen atom which still remains is then replaced by bromine in the customary manner.

Preferred salts of the compounds of the formula (I), from the viewpoint of phytotoxicity or toxicity to animals, are salts with physiologically acceptable acids. These include, preferably, salts with the hydrogen halide acids, such as, for example, hydrochloric acid and hydrobromic acid, in particular hydrochloric acid, phosphoric acid, nitric acid, monofunctional and bifunctional carboxylic acids and hydroxycarboxylic acids, such as, for example, acetic acid, citric acid, sorbic acid and lactic acid, and 1,5-naphthalenedisulphonic acid. Said acids, of course, also form pharmaceutically acceptable salts; additional acids which form pharmaceutically acceptable salts include lactic, ascorbic, maleic, salicyclic, aminosalicylic, nicotonic, methanesulfonic, ethanesulfonic, methionine, tryprophan, lysine, arginine, etc.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Possible diluents for use in the process according to the invention for preparing the compounds of formula I, are preferably inert organic solvents. These include, preferably, ketones, such a diethyl ketone and, in particular, acetone and methyl ethyl ketone; nitriles particularly alkanoic acid nitriles having 2 to 6 carbon atoms, such as propionitrile and, in particular, acetonitrile; alcohols, particularly alkanols having 1 to 6 carbon atoms such as ethanol or isopropanol; ethers, such as tetrahydrofurane or dioxane; optionally substituted aromatic (particularly mono- or bi-cyclic carbocyclic) hydrocarbons, such as benzene, toluene and halogenated, especially chlorinated aromatic hydrocarbons, such as chlorobenzene 1,3-dichlorobenzene, etc. formamides, such as, in particular, dimethylformamide; and halogenated or diethylformamide particularly chlorinated aliphatic hydrocarbons, such as chlorinated alkanes having up to carbon atoms, for example, methylene chloride, carbon tetrachloride or chloroform.

The process for preparing the compounds of formula I is carried out in the presence of an acid-binding agent. It is possible to use any of the inorganic or organic acid-binding agents which can customarily be used, such as alkali metal carbonates, for example sodium carbonate, potassium carbonate and sodium bicarbonate, or such as lower tertiary alkylamines having up to 12 carbon atoms, cycloalkylamines having up to 12 ring members or aralkylamines, particularly monocyclic or bicyclic carbocyclic aralkyl amines wherein the alkyl portion has 1 to 4 carbon atoms (preferably 1 to 2 carbon atoms), for example triethylamine, N,N-dimethylcyclohexylamine, dicylcohexylmethylamine and N,N-dimethylbenzylamine, or furthermore pyridine and diazabicyclooctane. An excess of imidazole is preferably used.

The reaction temperature used can be varied within a relatively wide range. In general, the reaction is carried out at from about 0° to about 150° C., preferably at from 60° to 120° C., usually in the presence of a solvent, such as acetone or methyl ethyl ketone.

In carrying out the above process for preparing compounds of formula I, from 1 to 2 mols of azole and from 1 to 2 mols of acid-binding agent are preferably employed per 1 mol of the compounds of the formula (II). Isolation of the compounds of the formula (I), may be effecting by distilling off diluent, taking up the residue in an organic solvent and washing with water and resulting solution. The organic phase may then be dried over sodium sulphate and freed from the solvent in vacuo. The residue may be purified by distillation or recrystallisation.

In the case where the process for the preparation of a compound of formula I includes a reduction step, suitable diluents for this step are polar organic solvents. These include, preferably, alcohols, such as methanol, ethanol, butanol and isopropanol, and ethers, particularly dialkyl ethers having 2 to 12 carbon atoms, such as diethyl ether dioxane or tetrahydrofurane. In general, the reduction is carried out at from 0° to about 30° C., preferably at 0° to about 20° C. For the reaction, generally about 1 mol of a borohydride (or equivalent reducing agent) such as sodium borohydride or lithium borohydride, is employed per 1 mol of the compound of the formula (II). Isolation of the compounds of the formula (I) after reduction may be effected by taking up the residue in, for example, dilute hydrochloric acid and rendering the resulting solution alkaline and then extracting with an organic solvent. Alternatively only water may be added and the resulting mixture extracted by shaking with an organic solvent. The mixture may then be further worked up by conventional techniques.

Examples which may be mentioned of particularly active representatives of the active compounds of formula I according to the invention, in addition to those of the Preparation Exampls and the Examples in Table 1, are the following: 1-(2-chlorophenoxy)-2-(2,4-dichlorophenyl)-1-(imidazol-1-yl)-ethan-2-one and -ol, 1-(2-isopropylphenoxy)-2-(2,4-dichlorophenyl)-1-(imidazol-1-yl)-ethan-2-one and -ol, 1-(2-methylphenoxy)-2-(2,4-dichlorophenyl)-1-(imidazol-1-yl)-ethan-2-one and -ol and 1-(2-chloro-4-methylphenoxy)-2-(2,4-dichlorophenyl)-1-(imidazol-1-yl)-ethan-2-one and -ol.

The compounds of the formula (I), which can be used according to the invention, and their salts, show antimicrobial, in particular powerful antimycotic effects. They possess a very broad spectrum of antimycotic activity, especially against dermatophytes and blastomyces as well as biphase fungi, for example against varieties of Candida, such as *Candida albicans,* varieties of Epidermophyton, such as *Epidermophyton floccosum,* varieties of Aspergillus, such as *Aspergillus niger* and *Aspergillus fumigatus,* varieties of Trichophyton, such as *Trichophyton mentagrophytes,* varieties of Microsporon, such as *Microsporon felineum* and varieties of Penicillium, such as *Penicillium commune.* The recital of these micro-organisms in no way implies a limitation of the germs which can be combated but is only of illustrative character.

The following may be mentioned as examples of fields of indication in medicine: dermatomycoses and systemic mycoses especially those caused by Trichopyton mentagrophytes and other varieties of Trichlphyton, varieties of Microsporon, *Epidermophyton floccosum,* blastomyces and biphase fungi as well as moulds.

The present invention also provides fungicidal compositions useful as fungitoxic compositions containing as active ingredient a compound of the formula (I), or a salt thereof, in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the formula (I), or a salt thereof, alone or in admixture with a diluent or carrier.

Preferably, in formula (I), X represents fluorine, chlorine, bromine, iodine, straight-chain or branched alkyl with 1 to 4 carbon atoms, or phenyl which is optionally substituted by halogen (especially chlorine) and n represents 0, 1 or 2.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention. "Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formedinto tablets, dragees, capsules and pills include the following:

(a) fillers and extenders, e.g. starch, sugars, mannitol, and silicic acid;

(b) binding agents, e.g. carboxymethyl cellulose and other cellulose derivatives, alginates, gelatine and polyvinyl pyrrolidone;

(c) moisturizing agents, e.g. glycerol;

(d) disintegrating agents, e.g. agar-agar, calcium carbonate and sodium bicarbonate;

(e) agents for retarding dissolution e.g. paraffin;

(f) resorption accelerators, e.g. quaternary ammonium compounds;

(g) surface active agents, e.g. cetyl alcohol, glycerol monostearate;

(h) absorptive carriers, e.g. kaolin and bentonite;

(i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is from 0.5 to 15 g. preferably from 2.5 to 10 g. of active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), rectally or locally, preferably parenterally especially intravenously. Preferred pharmaceutical compositions and medicaments are therefore those adapted for intravenous administration, such as sterile and blood-isotonic solutions and emulsions and ampoules containing them. Administration in the method of the invention is preferably intravenously.

In general it has proved advantageous to administer amounts of from about 10 mg. to 300 mg/kg of body weight most preferably from about 50 to 200 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, whilst other cases the upper limit mentioned must be exceeded to achieve the desired results. Where larger amounts are administered it can be advisable to divide these into several individual administrations over the course of the day.

EXAMPLE A

Anti-Mycotic in vitro activity

Description of the experiment:

The in vitro tests were carried out in a series dilution test with germ inocula of an average of $5 \times 10^4$ germs/ml of substrate. The nutrient medium was (a) for dermatophytes and moulds: Sabouraud's milieu d'épreuve and (b) for yeasts: meat extract/glucose broth.

The incubation temperature was 28° C. and the duration of incubation was 24 to 96 hours.

The results of the tests of the activity of various compounds of the invention against diverse micro-organisms are given in the following Table A.

EXAMPLE B

Antimycotic in vivo activity (oral) in candidosis of mice

Description of the experiment:

Mice of the type SPF-CF$_1$ were infected intravenously with $1-2 \times 10^6$ logarithmically growing Candida cells, which were suspended in physiological sodium chloride solution. The animals were treated orally one hour before and seven hours after the infection with, in each case, 100 mg/kg of body weight of the formulations.

Untreated animals died from the infection 3 to 6 days after infection. The survival rate on the 6th day after infection was about 5% in the case of untreated control animals.

Explanation of symbols:

$+++++$ = very good action = $\geq 90\%$ of survivors on the

Table A

Anti-mycotic in vitro activity
MINIMUM INHIBITORY CONCENTRATION VALUES in γ/ml of nutrient medium for

| Active compound | Trichophyton mentagr. | Candida albicans | Penicillium commune | Aspergillus species | Microsporon felineum | Torulopsis glabrata |
| --- | --- | --- | --- | --- | --- | --- |
| $O_2N$—⟨⟩—O—CH—CO—C(CH$_3$)$_3$ with imidazolyl (known) | 1 | 100 | 100 | 40 | 100 | — |
| C$_6$H$_5$-substituted, Cl-substituted phenyl—O—CH—CO—C(CH$_3$)$_3$ with imidazolyl (known) | 40 | 40 | 100 | >100 | >100 | — |
| Cl—⟨⟩—CH(OH)—CH(imidazolyl)—C(CH$_3$)$_3$ (known) | 8 | 64 | >64 | — | — | — |
| (CH$_3$)$_3$C—⟨⟩—O—CH(imidazolyl)—CH(OH)—C(CH$_3$)$_3$ (known) | 32 | >64 | >64 | >64 | — | — |
| 2,4,5-tri-Cl phenyl—O—CH(imidazolyl)—CO—⟨⟩ × HCl (known) | 1 | — | 100 | 40 | 100 | — |
| Cl—⟨⟩—O—CH(imidazolyl)—C(OH)$_2$—⟨⟩ × HCl (known) | 4 | — | 100 | 40 | 40 | — |
| (Compounds from Example No.) | | | | | | |
| 1 | <1 | 32 | 32 | 32 | 4 | 4 |
| 2 | <1 | 4 | 32 | — | 32 | 1 |
| 3 | <1 | 32 | 8 | 4 | 32 | 8 |
| 12 | <1 | 8 | 8 | 32 | 32 | 8 |
| 13 | <1 | 32 | 32 | — | 32 | 8 |

-continued

Explanation of symbols:

++++ = good action = ≧80% of survivors on the 6th day after infection
+++ = action = ≧60% of survivors on the 6th day after infection
++ = poor action = ≧40% of survivors on the 6th day after infection
+ = trace of action
n.a. = no action Table B
Antimycotic in vivo activity (oral) in candidosis of mice

| Active compound | Action |
|---|---|
| (known) Ph—Ph—O—CH(N-imidazolyl)—CO—C(CH$_3$)$_3$ | n.a. |
| (known) Ph—Ph—CH(OH)—CH(N-imidazolyl)—C(CH$_3$)$_3$ | n.a. |
| (Compounds from Example No.) | |
| 1 | +++++ |
| 2 | ++++ |
| 12 | ++ |

The active imidazolyl compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens.

They display a particularly good activity against parasitic fungi on above-ground parts of plants.

As plant protection agents, the active compounds according to the invention can be used with particularly good success for combating powdery mildew fungi, for example for combating powdery mildew of cucumbers (*Erysiphe cichoriacearum*), as well as against cereal diseases, for example cereal rust.

As plant protection agents, the compounds according to the invention can be used for the treatment of soil, for the treatment of seed and for the treatment of above-ground parts of plants.

The active compounds can be converted into the customary formulations for fungitoxic use, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

The active compounds according to the invention can be present in the formulations as a mixture with other active compounds, such as fungicides, insecticides, acaricides, nematicides, herbicides, bird repellants, growth factors, plant nutrients and agents for improving soil structure.

The formulations useful as fungitoxic agents in general contain from 0.1 to 95 percent by weight of active compound, preferably from 0.5 to 90 percent.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting, scattering, dry dressing, moist dressing, wet dressing, slurry dressing or encrusting.

Especially when used as leaf fungicides, the active compound concentrations in the use forms can be varied within a fairly wide range. They are, in general, from 0.00001 to 0.1 percent by weight, preferably from 0.0001 to 0.05 percent.

For treatment of seed, amounts of active compound of from 0.001 to 50 g per kilogram of seed, preferably from 0.01 to 10 g, are generally employed.

The present invention further provides crops protected from damage by fungi by being grown in areas in which immediately prior to and/or during the time of the growing a compound of the formula (I), or a salt thereof, was applied alone or in admixture with a diluent or carrier.

It will be seen that the usual methods of providing a harvested crop may be improved by the present invention.

The fungicidal activity of the compounds of this invention is illustrated by the following biotest Examples.

In these Examples, the compounds according to the present invention are each identified by the number (given in brackets) of the corresponding preparation Example below.

The known comparison compounds are identified as follows below:

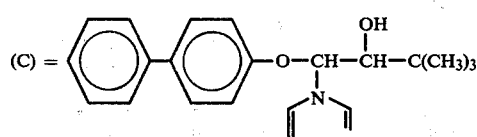

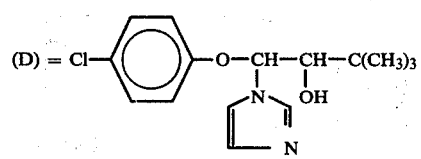

EXAMPLE C

Erysiphe test (cucumber)/protective

Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of solvent and the concentrate was diluted with the stated amount of water containing the stated amount of emulsifier.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus Erysiphe cichoriacearum. The plants were subsequently placed in a greenhouse at 23°–24° C. and at a relative atmospheric humidity of about 75%.

After 12 days, the infection of the cucumber plants was determined. The assessment data were converted to percent infection. 0% meant no infection; 100% meant that the plants were totally infected.

The active compounds, the concentrations of the active compounds and the results can be seen from the following table C:

The known comparison compound is identified as follows:

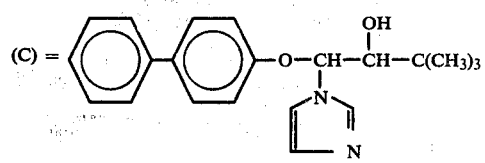

Table C

| Erysiphe test (cucumbers)/protective | |
|---|---|
| Active compound | Infection in % at an active compound concentration of 0.00025% |
| (C) | 91 |
| (2) | 34 |
| (13) | 71 |

EXAMPLE D

Shoot treatment test/cereal rust (leaf-destructive mycosis)/protective

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of Puccinia recondita in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80–90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The active compound was the more active, the lower was the degree of rust infection.

The active compounds, active compound concentrations in the spray liquor and degrees of infection can be seen from the following table D.

The known comparison compounds are identified as follows:

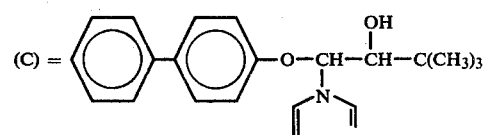

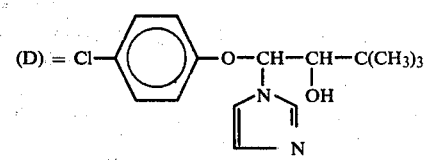

Table D

Shoot treatment test/cereal rust/protective

| Active compounds | Active compound concentration in the spray liquor in % by weight | Infection in % of the untreated control |
|---|---|---|
| untreated | — | 100 |
| (D) | 0.025 | 50.0 |
| (C) | 0.025 | 58.8 |
| (4) | 0.025 | 23.8 |
| (5) | 0.025 | 23.8 |
| (12) | 0.025 | 33.8 |
| (13) | 0.025 | 25.0 |

PREPARATION EXAMPLES

Example 1

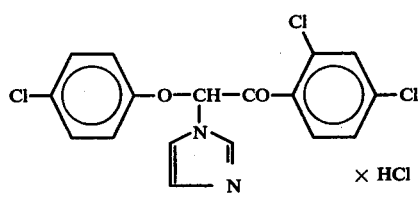

103 g (0.26 mol) of 1-bromo-1-(4-chlorophenoxy)-2-(2,4-dichlorophenyl)-ethan-2-one are added dropwise, at the boil, to 65 g (1 mol) of imidazole in 650 ml of acetonitrile. The mixture is heated under reflux for 40 hours. Thereafter, the solvent is distilled off in vacuo, the residue is taken up in 500 ml of methylene chloride and the methylene chloride solution is extracted by shaking four times with 250 ml of water each time. The organic phase is dried over sodium sulphate and concentrated by distilling off the solvent in vacuo. The residue is taken up in 1,000 ml of acetone, and 47 g (0.26 mol) of 1,5-naphthalenedisulphonic acid in 100 ml of acetone are added. The precipitate which forms is filtered off and boiled up with 100 ml of acetone. 200 ml of sodium bicarbonate solution and 500 ml of methylene chloride are added to the residue. The organic phase is separated off, washed with 200 ml of water and concentrated by distilling off the solvent in vacuo. The residue is taken up in 200 ml of ether and dry hydrogen chloride is added in excess. After distilling off the ether in vacuo, the oily residue is recrystallised from acetone. This gives 31.6 g (29% of theory) of 1-(4-chlorophenoxy)-2-(2,4-dichlorophenyl)-1-imidazol-1-yl-ethan-2-one hydrochloride of melting point 146°-148° C.

Example 2

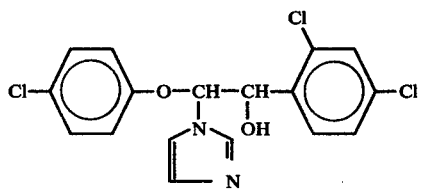

45.5 g (0.108 mol) of 1-(4-chlorophenoxy)-2-(2,4-dichlorophenyl)-1-imidazol-1-yl-ethan-2-one hydrochloride (Example 1) are dissolved in 100 ml of methanol and 4.32 g (0.108 mol) of sodium hydroxide are added. 4.5 g (0.12 mol) of sodium borohydride are added in portions at 0° to 5° C. and the mixture is stirred for 15 hours at room temperature. 60 ml of concentrated hydrochloric acid are then added dropwise at 0° C., and the mixture is again stirred for 15 hours at room temperature. The reaction mixture is then stirred into 800 ml of saturated sodium bicarbonate solution and extracted by shaking with 500 ml of methylene chloride. The organic phase is dried over sodium sulphate and concentrated by distilling off the solvent in vacuo. The residue is recrystallised from ether. This gives 30 g (72.5% of theory) of 1-(4-chlorophenoxy)-2-(2,4-dichlorophenyl)-1-imidazol-1-yl-ethan-2-ol as an isomer mixture of melting point 108°-110° C.

The following compounds in Table 1 are obtained by methods analogous to those the Examples given above. In each instance, of course, the salt can be transformed into the free base by the standard, known methods referred to above.

Table 1

| Ex. No. | $X_n$ | A | Melting point (°C.) | |
|---|---|---|---|---|
| 3 | 2,4-$Cl_2$ | CO | 205–215 | (× HCl) |
| 4 | 4-(C₆H₄)-Cl | CO | 145–148 | (× HCl) |
| 5 | 4-(C₆H₅) | CO | 160–162 | (× HCl) |
| 6 | 4-F | CO | 160 | (× HCl) |
| 7 | — | CO | 162–168 | (× HCl) |
| 8 | 2,6-$Cl_2$ | CO | 180 | (× HCl) |
| 9 | 3-Cl | CO | 168–171 | (× HCl) |
| 10 | 4-$CH_3$ | CO | 110 | (× HCl) |
| 11 | 4-Cl,2-$CH_3$ | CO | 177–178 | (× HCl) |
| 12 | 2,4-$Cl_2$ | CH(OH) | 208–218 | (isomer mixture) (× HCl) |
| 13 | 4-(C₆H₅) | CH(OH) | 158–170 | (isomer mixture) (× HCl) |
| 14 | — | CH(OH) | 156–159 | (isomer mixture) (× HCl) |
| 15 | 3-Cl | CH(OH) | 165–167 | (isomer mixture) (× HCl) |

PREPARATION OF THE STARTING PRODUCTS

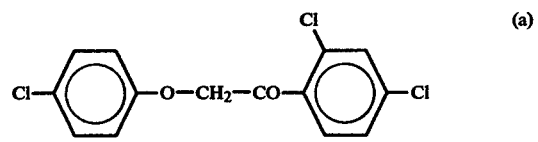

(a)

256 g (2 moles) of 4-chlorophenol were dissolved in 2 l of toluene and 280 g of potash (potassium carbonate) were added. The suspension was heated for 2 hours at a water separator, during which 200 ml of toluene distil off. Thereafter, 450 g (2 moles) of ω-chloro-2,4-dichloroacetophenone in 400 ml of toluene were added dropwise during refluxing, and the mixture was heated at the water separator for additional 12 hours. After cooling down the solution was washed once with 2 l of water, once with 1000 ml of a 10 percent solution of sodium hydroxide, and thereafter once with 2 l of water, and the toluene-phase was dried over sodium sulphate, and the solvent distilled off in vacuo of a water-jet pump. The crystalline residue was stirred up with 800 ml of ligroine, filtered with suction and dried. 448 g (71% of theory) of ω-(4-chlorophenoxy)-2,4-dichloroacetophenone of melting point 93°-95° C. were obtained.

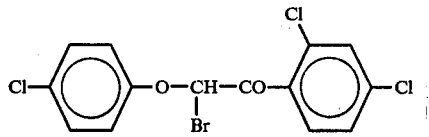
(b)

448 g (1.43 moles) of ω-(4-chlorophenoxy)-2,4-dichloroacetophenone were dissolved in 3 l of chloroform, 5 ml of ether saturated with hydrogen chloride were added and 75 ml of bromine were added dropwise in such a way that continuous decolorization could be observed. The mixture was stirred after the addition for 1 hour at 40° C. and the chloroform distilled off in vacuo of a water-jet pump. 572 g of raw 1-bromo-1-(4-chlorophenoxy)-2-(2,4-dichlorophenyl)-ethan-2-one were obtained, which might be used immediately for the reaction described in Example 1 above.

What is claimed is:

1. A 2,4-Dichlorophenyl-imidazolyl-ethanone or -ol of the general formula

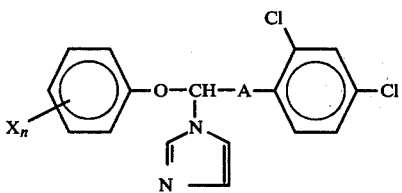

in which

A is a keto group or a CH(OH) group,

X is halogen, straight-chain or branched alkyl with 1 to 4 carbon atoms or phenyl optionally substituted by halogen, preferably chlorine, and n is an integer from 0 to 3, or an acid-addition salt thereof.

2. A compound according to claim 1 in which X is fluorine, chlorine, bromine, iodine, straight-chain or branched chain alkyl having 1 to 4 carbon atoms or phenyl optionally substituted by halogen and n is 0, 1 or 2.

3. A compound according to claim 1 which is 1-(4-chlorophenoxy)-2-(2,4-dichlorophenyl)-1-imidazol-1-yl-ethan-2-one hydrochloride.

4. A compound according to claim 1 which is 1-(4-chlorophenoxy)-2-(2,4-dichlorophenyl)-1-imidazol-1-yl-ethan-2-ol.

5. A pharmaceutical composition containing as an active ingredient an antimycotically effective amount of a compound according to claim 1 in admixture with a solid or liquefied gaseous diluent or in admixture with a liquid diluent other than a solvent of a molecular weight less than 200 except in the presence of a surface-active agent.

6. A pharmaceutical composition containing as an active ingredient an antimycotically effective amount of a compound according to claim 1 in the form of a sterile or isotonic aqueous solution.

7. A composition containing from 0.5 to 95% by weight of a compound of claim 1 together with an inert pharmaceutical carrier.

8. A medicament in dosage unit form comprising a compound according to claim 1 together with an inert pharmaceutical carrier.

9. A medicament of claim 8 in the form of tablets, pills, dragees, capsules, ampoules, or suppositories.

10. A method of combating mycoses in warm-blooded animals which comprises administering to the said animals an antimycatically effective amount of a compound according to claim 1 either alone or in admixture with a diluent or in the form of a medicament.

11. A method according to claim 10 in which the active compound is administered in an amount of 10 to 300 mg per kg body weight per day.

12. A method according to claim 10 in which the animals are ruminants.

13. A method according to claim 10 in which the active compound is administered orally.

14. A fungicidal composition comprising an effective amount of a compound of claim 1 or a salt thereof together with a physiologically tolerated acid.

15. A composition of claim 14 containing from 0.1 to 95% by weight of the said compound of claim 1.

16. A method of combating fungi which comprises applying to the fungi, or to a habitat thereof, a fungicidally effective amount of a compound or salt according to claim 1.

17. A method according to claim 16 in which a composition is used containing from about 0.00001 to 0.1% of the active compound, by weight.

18. A method according to claim 17 in which a composition is used containing from about 0.0001 to 0.5% of the active compound, by weight.

19. A method according to claim 16, in which the compound is applied to seed in an amount of about 0.001 to 50 g per kg of seed.

20. A method according to claim 19, in which the active compound is applied to seed in an amount of about 0.01 to 10 g per kg of seed.

* * * * *